(12) United States Patent
Faries, Jr. et al.

(10) Patent No.: US 6,548,728 B1
(45) Date of Patent: Apr. 15, 2003

(54) WOUND DRESSING GARMENT

(75) Inventors: Durward I. Faries, Jr., McLean, VA (US); Robert A. Bishop, II, Plano, TX (US)

(73) Assignee: Medical Products, Inc., Chantilly, VA (US)

( * ) Notice: Subject to any disclaimer, the term of this patent is extended or adjusted under 35 U.S.C. 154(b) by 0 days.

(21) Appl. No.: 09/635,919

(22) Filed: Aug. 10, 2000

(Under 37 CFR 1.47)

Related U.S. Application Data

(60) Provisional application No. 60/148,271, filed on Aug. 11, 1999.

(51) Int. Cl.$^7$ ................................................ A61F 13/00

(52) U.S. Cl. .............................. 602/42; 602/43; 602/54

(58) Field of Search ................................ 602/3, 41–59, 602/75; 2/311, 309; 24/422; 128/DIG. 15, 888, 889, 892

(56) References Cited

U.S. PATENT DOCUMENTS

| | | |
|---|---|---|
| 1,000,750 A | 8/1911 | Nerli |
| 2,069,643 A | 2/1937 | Burke |
| 2,653,601 A | 9/1953 | Morrison |
| 3,279,465 A | 10/1966 | Cherio et al. |
| 3,343,537 A | 9/1967 | Graham |
| 3,521,632 A | 7/1970 | Graham |
| 4,661,099 A | 4/1987 | Von Bittera et al. |
| 4,671,267 A | 6/1987 | Stout |

(List continued on next page.)

OTHER PUBLICATIONS

Exu–Dry–The Only Dressing with Anti–Shear Layer, Plastic Surgical Nursing, vol. 17, No. 4, Winter 1997.

Canderm Pharma Inc., Wound Care, Epi–Derm, printout of Aug. 13, 1998.

Spectragel, The Sheetless Keloid Scar Gel, For the Maintenance of Keloid & Hypertrophic Scars, printout of Aug. 13, 1998.

Kelo–Cote, A Revolutionary new form of gel sheeting without the sheet, Jul. 15, 1998.

Keloid Products, 1996.

DermaSof, Plastic Surgical Nursing, vol. 17, No. 4, Winter 1997.

Primary Examiner—Danton D. DeMille
Assistant Examiner—Quang D Thanh

(57) ABSTRACT

A wound dressing garment includes an outer structure layer formed of a pliable material and an interior lining formed of a self-adhesive gel material which serves as a dressing for directly contacting wounds such as burns on a patient. The structure layer provides the overall shape of the garment as well as a framework for supporting the gel layer. The structure layer has at least two edge portions that are securable (i.e., either permanently secured or detachably securable) to each other to provide a partial enclosure suitable for enveloping a portion of the body. The structure layer can include one or more layers of material and can be made of one or more of a variety of materials, such as fabric or elastomeric materials. The self-adhesive, sheet-like gel layer serves as an interior lining of the garment, such that gel layer presents an interior surface for directly contacting the skin of the patient. The gel layer has a soft, tacky texture and readily adheres to the skin but leaves no perceptible residue on the skin when removed. The gel material does not tend to significantly disturb newly formed tissue at the wound site when removed and essentially functions as a synthetic skin over the wound, allowing the wound to heal with a minimum of interaction with the external environment.

54 Claims, 2 Drawing Sheets

U.S. PATENT DOCUMENTS

| | | | | |
|---|---|---|---|---|
| 4,699,146 A | * | 10/1987 | Sieverding | 128/640 |
| 4,909,244 A | * | 3/1990 | Quarfoot et al. | 602/48 |
| 4,991,574 A | * | 2/1991 | Pocknell | 602/48 |
| 5,005,567 A | | 4/1991 | Gilman et al. | |
| 5,115,801 A | | 5/1992 | Cartmell et al. | |
| 5,156,601 A | | 10/1992 | Lorenz et al. | |
| 5,204,110 A | | 4/1993 | Cartmell et al. | |
| 5,328,449 A | | 7/1994 | Andrews et al. | |
| 5,425,702 A | * | 6/1995 | Carn et al. | 602/62 |
| 5,527,270 A | * | 6/1996 | Chase et al. | 602/41 |
| 5,643,189 A | | 7/1997 | Masini | |
| 5,682,617 A | | 11/1997 | Tumas | |
| 5,935,595 A | * | 8/1999 | Steen | 424/443 |
| 5,968,003 A | * | 10/1999 | Sisson | 602/75 |

* cited by examiner

WOUND DRESSING GARMENT

CROSS-REFERENCE TO RELATED APPLICATIONS

This application claims priority from U.S. Provisional Patent Application Serial No. 60/148,271, entitled "Wound Dressing Garment" and filed Aug. 11, 1999. The disclosure of that provisional application is incorporated herein by reference in its entirety.

BACKGROUND OF THE INVENTION

1. Field of the Invention

The present invention relates to a wound dressing garment shaped to conform to the contours of body parts and, more particularly, to a dressing garment lined with a self-adhesive sheet-like gel layer forming an inner surface that directly contacts the wound and skin.

2. Description of the Related Art

Various gel-like materials are known to have properties that promote the healing of wounds such as severe burns. Sheet-like wound dressings having a self-adhesive layer formed of a gel material have been used to treat skin wounds by placing the gel material in direct contact with the wound. These dressings are secured to the wound via adhesion of the gel material to healthy skin surrounding the wound. The gel materials are typically tacky to the touch and readily adhere to the skin, but are easily removed from the skin without significantly pulling the skin or disturbing or clinging to newly formed tissue at the wound site, and leave no perceptible residue. These gel materials tend to manage fluids seeping from the wound in a manner conducive to healing and can be used to deliver additives such as anti-microbial agents to the tissue of the wound to prevent infection. In effect, such gel layers operate to seal the wound and function as a synthetic skin.

For example, U.S. Pat. No. 4,661,099 to von Bittera et al., incorporated herein by reference in its entirety, discloses a self-adhesive sheet-like structure having a support layer and an adhesive polyurethane gel layer which adheres to the skin and leaves virtually no residue when removed. The sheet-like structure can be used as a wound dressing in which a gauze bandage is held in place on the wound by the polyurethane gel layer that adheres to the skin surrounding the wound. On dry wounds or wounds having only slight discharge, the polyurethane gel layer can be adapted for use in direct contact with the wound by chemically altering the gel to increase its absorbency.

U.S. Pat. No. 5,115,801 to Cartmell et al., incorporated herein by reference in its entirety, discloses a multi-layer burn dressing having a hydrogel material layer that is placed in direct contact with the burn site on the skin. The hydrogel serves as a bio-compatible, bacterial protective, fluid absorbing, cushioned skin-like medium that facilitates the healing process.

Silicone gel sheets have also been applied directly to damaged skin to treat burns and scars, as disclosed, for example, in U.S. Pat. No. 4,991,574 to Pocknell, incorporated herein by reference in its entirety. In particular, silicone gels have been found to prevent keloid and hypertrophic scaring at wound sites and to reduce the visibility of existing scars. Such silicone gels are manufactured, for example, by Applied Silicon Corporation.

The aforementioned gel dressings are universally produced in flat sheets, with the gel material layer typically being secured to at least a substrate layer providing structural integrity to the dressing. One problem with such dressings is that, while these flat sheets are generally pliable and can be molded to a degree to conform to skin contours, such flat sheets have a limited ability to cover highly contoured skin surfaces of the body, e.g., the face, the scalp, the neck, the shoulders, the hands, the complete torso and/or upper body and arm(s), the complete lower body and/or leg(s), bent elbows and knees, hips, ankles, and feet. Consequently, these sheet-like dressing are generally most suitable for covering only a limited skin area. Further, due to their sheet-like shape, these dressings cannot generally form a secured enclosure to envelop a body part and therefore must rely almost exclusively on the adhesion of the gel material to remain secured to the body.

To cover highly contoured portions of the body, it would be necessary to cut pieces of the sheet dressing to suitable sizes and shapes, and to cover the wound in sections with plural dressing pieces. The set of individual dressing pieces might imperfectly cover the wound, and the cutting and application of customized dressing pieces would be time consuming and would make rapid application of the dressing virtually impossible. Further, this cumbersome operation would have to be performed each time the dressing is changed.

Burn dressings that are shaped to conform to certain portions of the body have long been known in the field. These dressings typically employ conventional wound-contact materials that are absorbent and permeable to fluid and air, such as gauze and fabric. For example, U.S. Pat. No. 3,343,537 to Graham, incorporated herein by reference in its entirety, discloses burn dressings for covering various anatomical parts. The dressings consist of a porous, multi-layer silk lining which comes into contact with the wound, and a multi-layer gauze backing.

U.S. Pat. No. 3,279,465 to Cherio et al., incorporated herein by reference in its entirety, discloses a bandage in the form of a vest having two short sleeves. The bandage consists of a net-like material that holds gauze in place over the wound.

U.S. Pat. No. 5,328,449 to Andrews et al., incorporated herein by reference in its entirety, discloses a wound dressing in the shape of a glove having a porous skin-contacting layer, an absorbent intermediate layer, and a outer layer formed of a water-proof breathable material.

While both gel materials and dressing garments have been used for many years in the treatment of burns and other wounds, to date, no known attempts have been made to develop a dressing garment that employs a skin-contacting gel material. This may be due in part to the fact that sheet-like, gel-based dressings are rather thick, heavy and awkward in comparison to the thin, lightweight, fabric-like materials conventionally used to form dressing garments, and the appearance and gummy, resilient feel of such bulky gel-based dressing sheets do not readily suggest the fashioning of garments from these dressings. The fact that sheet-like, gel-based dressings are conventionally applied via adhesion to a limited skin area, rather than as an enclosure that surrounds or drapes over a body part, further contributes to the perception that sheet-like, gel-based dressings do not lend themselves to use in garments and that these dressings may be ill-suited and impractical for such applications.

Moreover, sheet-like, gel-based dressings are functionally unrelated to conventional burn garments. Sheet-like, gel-based dressings are substantially impermeable to air and moisture, and have limited or no absorbency. The gel material is designed to essentially seal the wound and functions substantially as a synthetic layer of skin over the wound, preventing any external interaction. In contrast, conventional burn garments are formed of permeable, absorbent materials that remove and absorb fluids exuded from the wound. Unlike a synthetic skin, such garments function more as a separate, external covering that rests over the wound and encourages healing of the wound by permitting a controlled flow of air to the wound and a controlled removal of fluid from the wound.

These structural and functional differences between sheet-like, gel-based dressings and conventional burn garments would explain, at least in part, why these wound treatments have existed side-by-side in the field for years without any consideration of possible applications of gel materials in garment-like dressings.

OBJECTS AND SUMMARY OF THE INVENTION

It is an object of the present invention to provide a wound dressing designed to surround or drape over a highly-contoured body part or a combination of adjacent body parts to bring a gel material layer in direct contact with a skin wound located on the body part(s).

It is a further object of the present invention to reduce the time required to apply a dressing to a highly contoured portion of the body and to avoid the need to form a customized dressing at the time the dressing is to be applied to the wound.

It is another object of the present invention to provide a wound dressing garment that is adjustable in size to fit a portion of the body for bodies in a range of sizes.

It is yet another object of the present invention to rely on the combination of adhesion and conformance to body shape to secure a wound dressing garment to the skin of a patient.

Another object of the present invention is to provide a wound dressing garment that can be placed on a portion of the body and removed with a minimum of movement of the body and a minimal need to slide the garment over the body.

Yet another object of the present invention is to provide a wound dressing garment that is easily modifiable to apply a gel-like dressing only to the portion of the body requiring treatment.

The aforesaid objects are achieved individually and in combination, and it is not intended that the present invention be construed as requiring two or more of the objects to be combined unless expressly required by the claims attached hereto.

According to the present invention, a wound dressing garment includes an outer structure layer formed of a pliable material and an interior lining formed of a self-adhesive sheet-like structure made of a gel material which serves as a dressing for directly contacting wounds such as burns on a patient. The structure layer provides the overall shape of the garment as well as a framework for supporting the gel layer. The structure layer has at least two edge portions that are securable (i.e., either permanently secured or detachably securable) to each other to provide a partial enclosure suitable for enveloping a portion of the body.

The structure layer can include one or more layers of material and can be made of one or more of a variety of materials, such as fabric or elastomeric materials. The structure layer may include plural panels that are permanently secured to each other (e.g., via stitching, fusing or adhesive) along seams. Edges of the structure layer that are detachably securable to each other can be secured using conventional fastening mechanisms, such as hook and loop fasteners.

The self-adhesive, sheet-like gel layer serves as an interior lining of the wound dressing garment and is coupled to an inner surface of the structure layer over at least a substantial portion of the garment, such that the gel layer presents an interior surface for directly contacting the skin of the wearer. The gel layer has a soft, tacky texture and readily adheres to the skin but leaves no perceptible residue on the skin when removed. The gel material does not tend to significantly disturb newly formed tissue at the wound site when removed. Essentially, the gel material functions as a synthetic skin over the wound, allowing the wound to heal with a minimum of interaction with the external environment. By way of example, the gel material can be a silicone gel, a hydrogel or a polyurethane gel.

The gel layer can be directly secured to the structure layer by the inherent self-adhesiveness of the gel material, and/or the gel and structure layers can be bonded together by pressure, heat, or a suitable adhesive. An intervening layer can be disposed between the structure layer and the gel layer to secure the structure and gel layers to each other. The intervening layer can be an elastomeric material to which the gel layer readily adheres. The structure layer can be attached to the opposite side of the intervening layer by an adhesive or other suitable means.

The gel layer is covered with a protective thin, peelable layer, such as a plastic film, to prevent the gel layer from accidentally contacting other surfaces. In operation, the peelable layer is peeled off of the gel layer just before applying the gel layer to the skin of the wearer.

In accordance with one embodiment of the present invention, the wound dressing garment is made adjustable in size to snugly fit body parts of patients in a range of body sizes by allowing the edge portions of the garment to be secured in an overlapped fashion. In particular, the edge portions of the gel layer are preferably separable from the corresponding edge portions of the structure layer, such that the edge portions of the gel layer can be overlapped separately from the structure layer. Stated differently, the overlapping edge portions of the gel layer and the structure layer can be interleaved such that both gel layer edge portions underlie both structure layer edge portions, with one gel layer edge portion being secured to the other gel layer edge portion (or its intervening backing layer) and the edge portions of the structure layer being secured to each other via fasteners.

The gel layer can be permanently detached from the structure layer in the edge region, or the gel layer can be detachable from the structure layer in the edge region by tugging or peeling apart the structure layer and the intervening layer. Optionally, the structure layer can be detachable over its entire inner surface from the gel layer and/or an intervening layer. If a particular wound does not require a gel layer over the entire extent of the garment, this detachability feature allows portions of the gel layer to be selectively removed to improve the comfort of the garment, while the entire structure layer remains intact to provide complete support for the gel layer and to preserve the ability of the structure layer to secure the garment to the body.

The wound dressing garment of the present invention can be formed to cover any portion of the body, including any one, combination, or portion of the following body parts: fingers, hands, wrists, elbows, shoulders, arms, the head, the scalp, the face and individual facial features, the neck, the torso, the waist, hips, the groin, legs, knees, ankles, feet, and toes. Thus, the wound dressing garment of the present invention can be any one, portion or combination of the following garments: a finger wrap, a glove, a mitt, a sleeve, a vest, a jacket, a mask, a skull cap, a neck tube, a girdle, shorts, pants, leggings, a leg wrap, a sock or a toe wrap.

The above and still further objects, features and advantages of the present invention will become apparent upon consideration of the following detailed description of specific embodiments thereof, particularly when taken in conjunction with the accompanying drawings wherein like reference numerals in the various figures are utilized to designate like components.

DETAILED DESCRIPTION OF THE PREFERRED EMBODIMENTS

Figure 1:
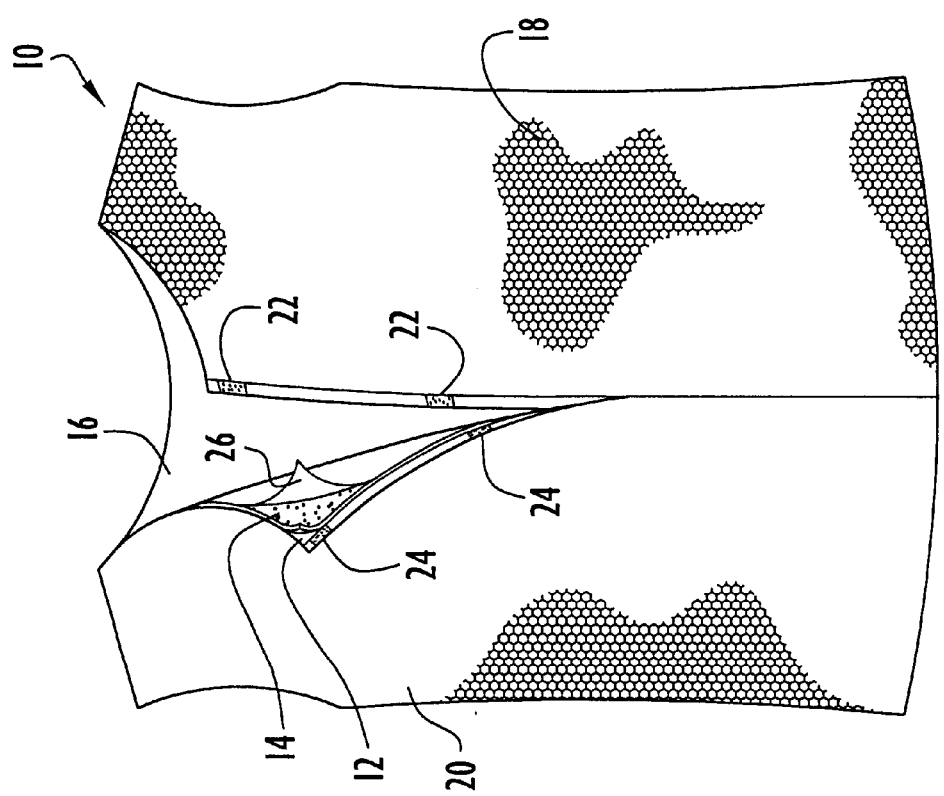
FIG. 1 is front view in elevation of a wound dressing garment for a human torso in accordance with an exemplary embodiment of the present invention.

Referring to FIG. 1, in accordance with an exemplary embodiment of the present invention, a wound dressing garment for treating wounds such as burns and scars takes the form of a sleeveless vest 10 that is shaped and sized to envelop the torso of the human body. As used herein, the term "envelop" means to substantially cover by enclosing, encasing, surrounding or fitting over a portion of the body, such that the correspondence between the shape of the garment and the covered portion of the body generally contributes to keeping the garment secured on the portion of the body. It will be understood that the term "envelop" does not require that an entire body part be covered; thus, for example, a portion of an arm can be enveloped while another portion of the arm or the hand can remain uncovered. It will be further understood that, while the wound dressing garment of the present invention is configured to envelop a portion or all of a body part or plural body parts, the wound dressing garment may include one or more openings for adjacent body parts (e.g., a torso wound dressing garment may include openings for the waist, neck and arms, and a glove-like wound dressing garment may include an opening for the arm). Thus, as used herein, the term "partial enclosure" refers to an enclosure that has at least one opening through which a body part adjacent the wound site can extend.

As shown in FIG. 1, exemplary garment 10 includes an outer structure layer 12 formed of a pliable material, and an inner lining gel layer 14 formed of a self-adhesive, sheet-like gel material suitable for treating wounds such as severe burns or scars. In the embodiment shown in FIG. 1, structure layer 12 is formed of a mesh fabric made of nylon or the like. Structure layer 12 provides the overall shape of the garment and provides a framework for supporting the gel layer 14.

The structure layer 12 of sleeveless vest garment 10 includes three mesh fabric panels sewn together at their edges. Specifically, garment 10 includes a back panel 16 sewn along part of one side edge and part of the top edge to a front left panel 18, and along part of another side edge and part of the top edge to a front right panel 20, leaving arm and neck openings between the panels. The edges of the panels that are sewn together have complementary shapes forming seams that correspond to contours of the portion of the body over which the seams of the garment fit (in this case, the shoulders and the sides of the torso).

In addition to providing the shape and framework of the garment, structure layer 12 supplements the gel layer 14 in securing the garment to the portion of the body (in this example, the torso). Specifically, front left and right panels 18 and 20 meet, but are not permanently attached, along a vertical (as worn on the body) centerline extending from the front center of the neck opening to the bottom of the garment at the front center of the waistline. Front left and right panels 18 and 20 are detachably securable to each other along the front vertical centerline with a fastener. The fastener can be any one or a combination of conventional fastening mechanisms, including, but not limited to: hook and loop fasteners, buckles, buttons, clasp or clipping mechanisms, snaps, straps with locking rings, zippers, string or fabric ties, straps or frictional force.

By way of example, the exemplary garment 10 shown in FIG. 1 includes complementary hook and loop fasteners 22 and 24 respectively attached to the corresponding edges of the left and right front panels of structure layer 12. Fasteners 22 and 24 engage each other to secure together the left and right front panels 18 and 20 along the front vertical centerline of garment 10. By securing the open edges of the structure layer 12 with fasteners, structure layer 12 forms a partial enclosure that augments the gel layer in keeping the garment securely attached to the body. Further, the detachability of the left and right front panels 18 and 20 allows the sleeveless vest garment 10 to be placed over and secured to the torso with a minimum of movement of the torso and garment 10 and with a minimum of contact between the torso and gel layer 14 of garment 10 prior to correctly positioning garment 10 on the torso.

As used herein and in the claims, the term "securable" is used broadly to describe both edge portions that are permanently secured to each other and edge portions that are detachably securable with fasteners. As will be understood from the foregoing description, structure layer 12 of garment 10 includes edges that are permanently secured to each other along seams as well as edges that are detachably securable to each other with fasteners. However, as will be evident from other embodiments described and shown herein, the present invention is not limited to embodiments of wound dressing garments having both permanently secured edges and detachably securable edges.

Self-adhesive, sheet-like gel layer 14 serves as an interior lining of garment 10 and is coupled to an inner surface of structure layer 12 over at least a substantial portion of the garment, such that gel layer 14 presents an interior surface for directly contacting the skin of the wearer. Gel layer 14 can be described as a soft, tacky, non-friable gel sheet that readily adheres to skin and that leaves no perceptible residue (e.g., no sticky or gummy residue) on the skin when removed. While described as sheet-like, it will be understood that the gel layer need not be planar, and may be curved or arcuate in one or more dimensions as required to conform to the shape of the garment. The gel material is slightly adhesive to skin, but does not tend to significantly disturb newly formed tissue at the wound site when removed. The gel material essentially functions as a synthetic skin over the wound, allowing the wound to heal with a minimum of interaction with the external environment. Optionally, additives such as anti-microbial agents, can be incorporated in the gel material to prevent infection of the wound.

The gel material of gel layer 14 can be, for example a semi-occlusive silicone gel, such as a silicone gel manufactured, for example, by Applied Silicon Corporation. Such silicone gels have been used in the treatment of burns and scars. Specifically, silicone gel sheeting has been found to improve wound healing, reduce pain, and produce a better cosmetic resulting by flattening and softening hypertrophic and keloid scar tissue and returning the skin to its natural color. Other suitable gel materials include hydrogels and polyurethane gels.

By way of non-limiting example, gel layer 14 can be approximately one-eighth to one-sixteenth of an inch in thickness or approximately one to five millimeters in thickness. It is to be understood that these dimensions are provided by way of example only and are not in any way limiting on the scope of the invention. Gel layer 14 can be secured to the interior surface of a structure layer 12 in a variety of ways. In the exemplary embodiment shown in FIG. 1, gel layer 14 directly contacts the nylon mesh structure layer 12 and is secured to structure layer 12, at least in part, by the inherent self-adhesiveness of the gel material. The bond between structure layer 12 and gel layer 14 can be formed by any one or a combination of: pressure (e.g., pressing the layers together), heat, and a suitable adhesive. The gel layer sheeting can be bonded to the panels of the structure layer prior to securing the panels together, or the panels of the structure layer 14 can be secured together prior to lining the garment with the gel layer 12. In either case, the gel layer 14 can comprise a plurality of sheets shaped and sized to line the desired portion of the garment. As explained in greater detail below, to provide maximum utility, the sheet or sheets of gel layer 14 preferably cover substantially all of the interior of the garment, with the gel layer 14 being separable or peelable from the structure layer so that selected portions of the gel layer 14 can be removed when not required to cover a particular wound.

Prior to application to the skin, gel layer 14 is covered with a protective thin, peelable layer 26, such as a plastic film, to prevent gel layer 14 from accidentally contacting other surfaces. In operation, peelable layer 26 is peeled off of gel layer 14 just before applying the gel layer to the skin of the wearer.

While shown in FIG. 1 as a nylon mesh fabric, the structure layer of the present invention is not limited to any particular material or combination of materials. The structure layer can comprise one or more layers formed of one or more materials, including, but not limited to: woven fabrics and textiles formed of natural and/or synthetic materials, non-woven fabrics and textiles formed of natural and/or synthetic materials, and elastomeric materials.

Figure 2:
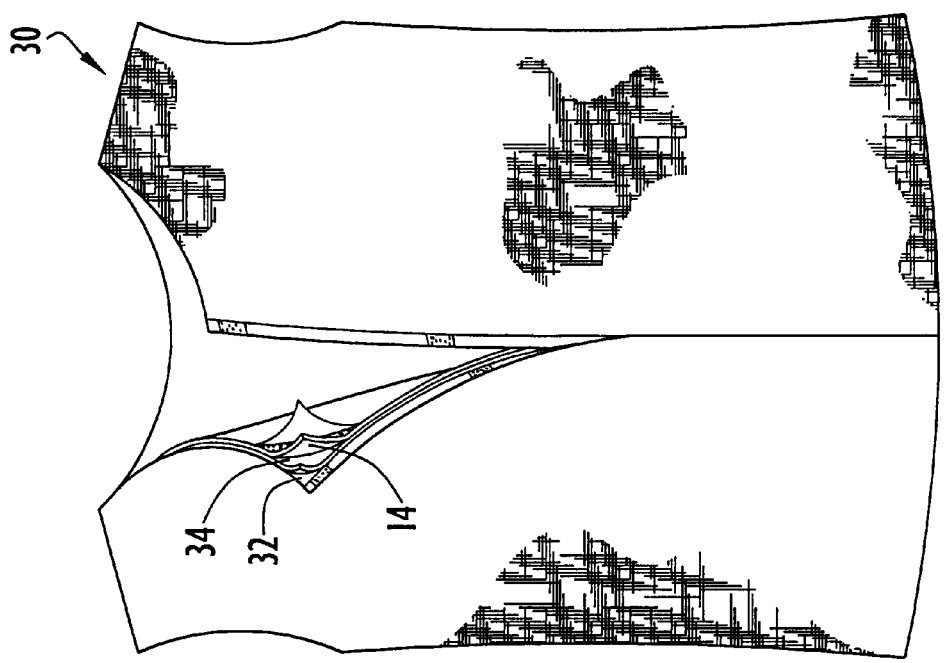
FIG. 2 is front view in elevation of a wound dressing garment for a human torso in accordance with another embodiment of the present invention.

Referring to FIG. 2, a wound dressing garment 30 in accordance with another embodiment of the present invention includes a structure layer 32 formed of a fabric material. Structure layer 32 and gel layer 14 are secured to each other via an intervening layer 34. Intervening layer 34 can be, for example, a galvanized or ungalvanized elastomeric material to which gel layer 14 readily adheres. Gel layer 14 is formed on one side of intervening layer 34, while structure layer 32 is attached to the other side of intervening layer 34 by glue or other suitable means. In addition to serving as a base layer to which structure layer 32 and gel layer 14 can be readily attached, intervening layer 34 also provides additional overall strength to the gel sheeting without significantly reducing the flexibility of the gel sheeting.

It will be readily understood that other structure layer configurations fall within the scope of the invention. For example, the structure layer can comprise any number of layers, or the structure layer can be formed of a single elastomeric layer without any fabric layers. In accordance with another embodiment, the structure layer is formed using a molding technique, wherein the structure layer comprises a material shaped by setting in a mold.

Where the structure layer includes a plurality of panels permanently secured to each other along seams (see FIGS. 1–3 and 5), the panels of the structure layer can be secured along the seams by sewing, stitching, staples or any other suitable mechanism. For example, where the panels of the structure layer comprise an elastomeric or thermoplastic material, the panels can be secured at their edges by heat fusing.

Figure 3:
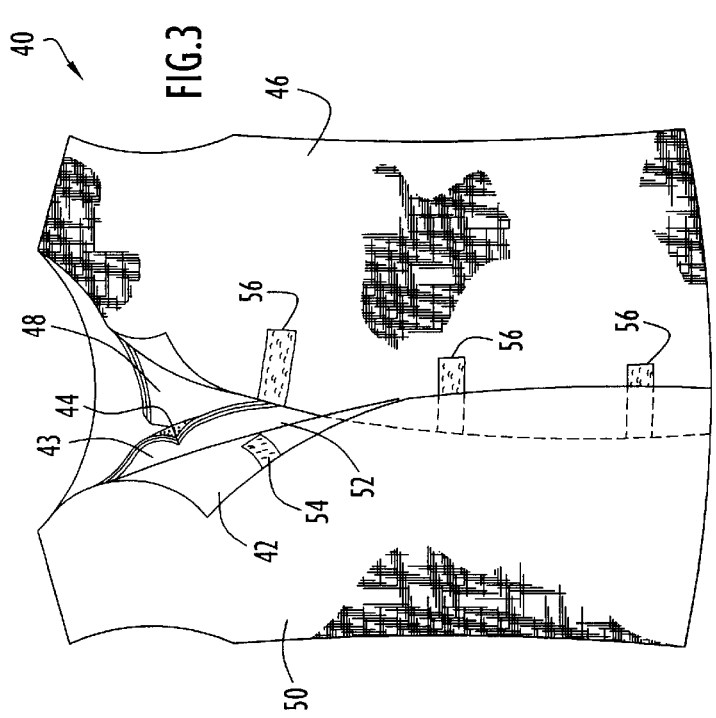
FIG. 3 is front view in elevation of an adjustable wound dressing garment for a human torso in accordance with another embodiment of the present invention.

In accordance with another embodiment of the present invention, a wound dressing garment is adjustable in size to snugly fit body parts in a range of sizes. Referring to FIG. 3, an adjustable wound dressing garment 40 for the torso includes a structure layer 42, an intervening elastomeric layer 43 and an inner gel layer 44. These layers are similar to those shown in FIG. 2, except that the intervening elastomeric layer 43 and gel layer 44 are detached or detachable from the structure layer 42 at least in the vicinity of the edges of the structure layer that are securable with fasteners. Specifically, a front left panel 46 of the structure layer 42 is detached from the edge portion 48 of the underlying intervening and gel layers 43 and 44 along the entire vertical edge of the front left panel over a distance of at least an inch, and preferably at least two inches, in the horizontal direction. Similarly, a front right panel 50 of the structure layer 42 is detached from the edge portion 52 of the underlying intervening and gel layers 43 and 44 along the entire vertical edge of the front right panel over a distance of at least an inch, and preferably at least two inches, in the horizontal direction. As seen in FIG. 3, gel layer edge portions 48 and 52 are essentially flaps in the shape of vertical strips extending along the front vertical centerline of garment 40 in parallel with edges of the structure layer 42. The overall size of the garment is selected to be at least as large as necessary to cover the torso of a wearer, such that, when the gel layer 44 is smoothly attached to the skin of the torso, the left and right edge portions 48 and 52 of the gel layer 44 overlap along the front vertical centerline of the garment. For example, the right edge portion 52 of the intervening and gel layers 44 overlaps and extends over the left edge portion 48, but extends underneath the left front panel 46 of structure layer 42. The overlying right edge portion 52 of the gel layer 44 readily adheres to the left edge portion 48 of the underlying intervening layer 43, thereby snugly sealing the gel layer 44 to the torso (alternatively, the overlapping portion of the edge portion can be trimmed off).

The detached portions of the left and right front panels 46 and 50 of the structure layer 42 also form overlapping flaps. In the foregoing example, the edge portion (flap) of the right front panel 50 overlaps and extends over the edge portion of the left front panel 46. A set of adjustable fasteners 54 and 56 respectively attached to the left and right front panels 46 and 50 are used to secure the edge portions of the front panels to each other in the overlapped position. By way of non-limiting example, fasteners 54 and 56 can be complementary hook and loop fasteners. To account for variation in the degree of overlap, the fasteners of at least one of the sets of fasteners 54 and 56 extend longitudinally in the horizontal direction (i.e., transversely of the garment body) to permit engagement of the fasteners over a range of overlap positions. In the preferred embodiment, the fasteners are rectangular. Adjustable length straps or any other type of adjustable position fasteners can be used with adjustable garment 40.

The adjustability of the wound dressing garment permits a wide range of body sizes to be fit with a limited number of different-sized garments (e.g., small, medium, large, extra large).

As will be understood from the foregoing, an important aspect of the adjustable wound dressing garment of this embodiment of the present invention is the region of detachment between the outer structure layer and the inner gel layer in the vicinity of the edges of the structure layer that are secured via fasteners. This detachment region permits both the gel layer and the structure layer to be independently overlapped and independently secured to provide a superior fit. Specifically, the overlapping portion of the gel layer can slide underneath the opposing edge of the structure layer and adhere directly to the opposing (overlapped) gel layer or the elastomeric backing of the gel layer. That is, a first gel layer edge portion can be interleaved between a second, opposing gel layer edge portion and a second, opposing structure layer, with the second structure layer being interleaved between the first gel layer edge portion and its corresponding first structure layer. Further, the two edges of the structure layer can be overlapped and fastened to each other without interference from the gel layer, thereby permitting a simple fastener design.

While described as having both left and right detached gel layer flaps, it will be understood that a similar result can be obtained by forming a detached gel layer flap along only one of the left and right edges of the front panels. In this case, independent overlapping is achieved by extending a first structure layer edge portion and its attached first gel layer edge portion between a second gel layer edge portion and a second structure layer edge portion that has been separated from the second gel layer edge portion.

The gel layer can be permanently detached (i.e., separated) from the structure layer in the edge region, or the gel layer can be detachable from structure layer in the edge region (as used herein and in the claims, the term "separable" is used broadly to describe both permanently detached edge portions and detachable edge portions or layers). Specifically, outer structure layer 42 can be peelable from intervening layer 43 at least in the vicinity of the front vertical centerline edges of garment 40. Preferably, a significant degree of tugging force is required to tug or peel apart structure layer 42 and intervening layer 43 so that these layers are not readily susceptible to being unintentionally detached.

Optionally, the structure layer can be detachable over its entire inner surface from the gel layer (or an intervening layer). If a particular wound does not require a gel layer over the entire extent of the garment, this detachability feature allows portions of the gel layer to be selectively removed to improve the comfort of the garment, while the entire structure layer remains intact to provide complete support for the gel layer and to preserve the ability of the structure layer to secure the garment to the body.

According to another embodiment of the adjustable wound dressing garment, the structure layer and the gel layer are not detached, and both the structure layer and gel layer of one edge of the garment overlap and extend over the structure layer of the other edge of the garment, and adjustable fasteners, such as straps, secure the exterior of the garment. While this embodiment may be simpler in some respects, the overlapping portion of the gel layer may have only limited adhesion to the underlying structure layer, and the design of the adjustable fasteners may be limited by absence of a structure layer flap detached from the gel layer.

While the wound dressing garment of the present invention has been shown in FIGS. 1–3 as a sleeveless vest for covering the torso, it will be understood that the present invention includes wound dressing garments that cover any portion of the body, including, but not limited to, any one, combination, or portion of the following body parts: fingers, hands, wrists, elbows, shoulders, arms, the head, the scalp, the face and individual facial features, the neck, the torso, the waist, hips, the groin, legs, knees, ankles, feet, and toes. Thus, the wound dressing garment of the present invention may take a number of different forms, including, but not limited to: a finger wrap, a glove, a mitt, a sleeve, a vest, a jacket, a mask, a skull cap, a neck tube, a girdle, shorts, pants, leggings, a leg wrap, a sock or a toe wrap.

Figure 4:
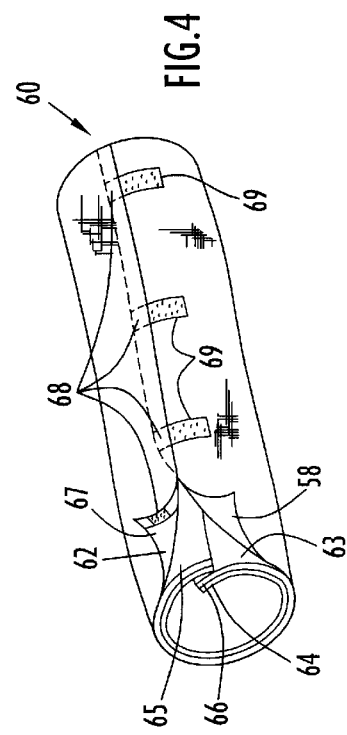
FIG. 4 is a perspective view of an adjustable wound dressing garment for a human arm in accordance with another embodiment of the present invention.

Referring to FIG. 4, an adjustable wound dressing garment in the form of a sleeve 60 for treating wounds on an arm is shown. Sleeve 60 includes an outer structure layer 62, an intervening elastomeric layer 63 and an inner gel layer 64. Structure layer 62 is formed of a pliable material, such as one or more of the above-described structure layer materials. Structure layer 62 comprises a single, generally rectangular panel which wraps around the arm, with longitudinal edges that meet or overlap along a line extending generally along the length of the arm. Structure layer 62 can also be formed from plural panels. The intervening elastomeric layer 63 and gel layer 64 are detached or detachable from the structure layer 62 at least in the vicinity of the longitudinal edges of the structure layer 62.

Specifically, a first longitudinal edge portion 66 of structure layer 62 is detached from the edge portion 58 of the underlying intervening and gel layers 63 and 64, and a second longitudinal edge portion 65 of structure layer 62 is detached from the edge portion 67 of the underlying intervening and gel layers 63 and 64. The structure layer edge portions 66 and 65 overlap with the gel/intervening layer edges 58 and 67 in an interleaved manner, much like the edges portions of the vest garment shown in FIG. 3. Specifically, the second gel/intervening layer edge portion 65 extends over first gel/intervening layer edge portion 66 but beneath first structure layer edge portion 58 (i.e., between edge portions 66 and 58), and the first structure layer edge portion extends over the second gel/intervening layer edge portion 65 and the second structure layer edge portion 67 (i.e., between edge portions 65 and 67).

Fasteners 68 and 69 are attached to the longitudinal edges of the structure layer 62 to enable the longitudinal edges to be secured to each other in an overlapped manner. By way of non-limiting example, fasteners 68 and 69 can be complementary hook and loop fasteners. To account for variation in the degree of overlap, the fasteners of at least one of the sets of fasteners 68 and 69 have a rectangular shape, extending longitudinally in the horizontal direction to permit engagement of the fasteners over a range of overlap positions.

The wound dressing sleeve 60 shown in FIG. 4 is an example of a wound dressing garment of the present invention having a structure layer with edge portions detachably secured to each other with fasteners, but with no edges permanently secured to each other along seams. Other embodiments of the present invention may include a structure layer with only permanently secured edges and no detachably securable edges. For example, a glove or mitten (not shown) to be fitted over the hand can include an inner gel layer lining and an outer structure layer formed of two or more panels sewn together, with a single opening for the wrist/arm (with no edges detachably securable with fasteners).

Figure 5:
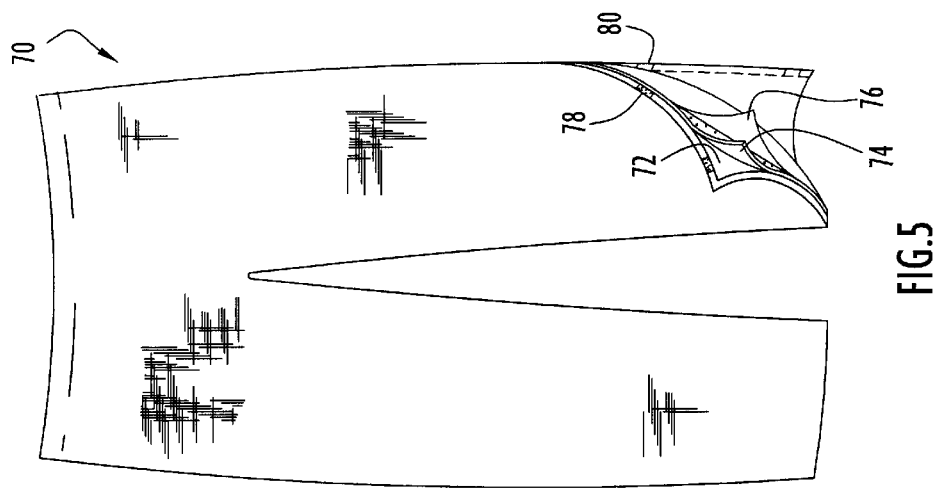
FIG. 5 is a front view in elevation of a wound dressing garment for the lower body in accordance with another embodiment of the present invention.

Referring to FIG. 5, according to yet another embodiment of the present invention, a wound dressing garment 70 in the form of leggings for covering wounds below the waist and on the legs is shown. Leggings 70 include an outer structure layer 72 formed of a pliable material, and an inner lining gel layer 74 formed of a self-adhesive, sheet-like gel material. Gel layer 74 is covered with a protective thin, peelable layer 76, such as a plastic film, to prevent gel layer 74 from accidentally contacting other surfaces prior to application to the wound.

Structure layer 74 is formed of a number of panels that are seamed together in much the same way as conventional pants or trousers. However, to avoid the need to slide the leggings over the legs and hips, the leggings are preferably detachably securable along the outseam of each leg portion of leggings 70. For example, as shown in FIG. 5, the front left leg panel is detachably securable to the back left leg panel along the left outseam with fasteners, such as complementary hook and loop fasteners 78 and 80 respectively attached to the corresponding edges of the front and back left leg panels. Although not explicitly shown in FIG. 5, the front and back right leg panels of leggings 70 can also be detachably securable along the right outseam. If only a selected portion of the lower body requires treatment with a wound dressing, unnecessary portions of the leggings can be removed or cut off from the portion applied to the wound. For example, if only the left leg requires the dressing, the gel layer 74 can be removed from leggings over all but the left leg portion of the leggings (leaving intact the structure layer), or the left leg portion of the leggings (both the structure layer and the gel layer) can be completely detached (e.g., by cutting) from the rest of the leggings.

It will be appreciated that the embodiments described above and illustrated in the drawings represent only a few of the many ways of implementing a wound dressing garment.

The garments described above may be applied to any portions of a human or animal body for any type of wound, sensitive area or for promotion of healing. The garments may be of any size or shape to accommodate any portions of bodies or any sized users. The garments can be formed to cover any portion of the body, including any one, combination, or portion of the following body parts: fingers, hands, wrists, elbows, shoulders, arms, the head, the scalp, the face and individual facial features, the neck, the torso, the waist, hips, the groin, legs, knees, ankles, feet, and toes. Thus, the wound dressing garment of the present invention can be any one, portion or combination of the following garments: a finger wrap, a glove, a mitt, a sleeve, a vest, a jacket, a mask, a skull cap, a neck tube, a girdle, shorts, pants, leggings, a leg wrap, a sock or a toe wrap. The vest may further include openings or wound dressing garments for other body portions (e.g., sleeves, a neck portion, leg portions, etc.). The garments may include any quantity of panels of any shape or size fastened together at any suitable locations by any conventional or other fastening techniques or mechanisms (e.g., sewing, stitching, staples, heat fusing where the panels of the structure layer comprise an elastomeric or thermoplastic material, etc.). The garments may be of the pullover type, or be detachable at any locations to permit placement over body portions. The garments may include any quantity of any type of conventional or other fasteners (e.g., hook and loop fasteners, buckles, buttons, clasp or clipping mechanisms, snaps, straps with locking rings, zippers, string or fabric ties, straps or frictional force, etc.) disposed at any locations to secure the garment about a body portion. The edges of the garments may overlap and be secured in any manner to facilitate placement of the garment over a body portion. In addition, the garments may be adjustable and, by way of example, include fasteners or straps that enable adjustment of the garment to accommodate various sized users or body portions.

The structure layer of the garments may include any quantity of layers of any suitable materials (e.g., nylon mesh, woven fabrics and textiles formed of natural and/or synthetic materials, non-woven fabrics and textiles formed of natural and/or synthetic materials, elastomeric materials, etc.). The intervening layer of the garments may include any quantity of layers of any suitable materials (e.g., a galvanized or ungalvanized elastomeric material or other material to which the gel layer may adhere, etc.). The protective layer of the garments may similarly include any quantity of layers of any suitable materials (e.g., plastic film, etc.). The structure, intervening and protective layers of the garments may be of any shape or size having any desired thickness.

The gel layer of the garments may be disposed on any portions or quantity of portions of the structure and/or intervening layers. The gel layer may be disposed on the garments via any conventional or other fastening techniques (e.g., by the inherent self-adhesiveness of the gel material, pressure (e.g., pressing the layers together), heat, suitable adhesive, etc.). The gel layer can be bonded to the panels of the structure layer prior to securing the panels together, or the panels of the structure layer can be secured together prior to lining the garments with the gel layer. The gel layer of the garments may be secured to and detachable from any portion or portions of the structure and intervening layers. The gel layer may include any quantity of segments of any shape or size disposed at any suitable locations within the garments. The gel layer may include any anti-microbial or other agents (e.g., medicinal, ointments, lotions, etc.), and may be implemented by a silicone gel, hydrogel, polyurethane gel or other suitable materials. The gel layer may have any degree of self-adhesiveness (e.g., including no or minimal self-adhesive properties).

It is to be understood that the terms "left", "right", "front", "back", "rear", "lop", "bottom", "upper", "lower", "horizontal", "vertical", "height", "length", "width", "thickness" and the like are used herein merely to describe points of reference and do not limit the present invention to any particular configuration or orientation.

Having described preferred embodiments of a new and improved wound dressing garment, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A wound dressing garment for promoting the healing of skin wounds, comprising:

a structure layer formed of a pliable material to envelope a body portion including an external skin wound to dress that wound and promote healing, said structure layer including an inner surface that faces generally toward the skin of the wearer when the garment is worn on the body and first, second, third and fourth edge portions, wherein at least the first and second edge portions are securable to each other to provide a partial enclosure suitable for enveloping said body portion; and a self-adhesive gel layer suitable for directly contacting said external skin wound to promote said healing, said gel layer being coupled to said structure layer and serving as said inner surface to form an interior surface of the garment;

wherein said gel layer is separable from said structure layer along at least one of the third and fourth edge portions of said structure layer, such that edge portions of said gel layer and the third and fourth edge portions of said structure layer are independently overlappable and, when the edge portions of said gel layer are overlapped and the third and fourth edge portions of said structure layer are secured to each other in an overlapped fashion, both the third and fourth edge portions of said structure layer overlay the edge portions of said gel layer.

2. The wound dressing garment of claim 1, wherein said first and second edge portions are permanently secured together along a seam in a substantially non-overlapping manner.

3. The wound dressing garment of claim 2, wherein said structure layer comprises at least a first panel having said first edge portion and a second panel having said second edge portion.

4. The wound dressing garment of claim 2, wherein said structure layer comprises a fabric material, and said first and second edge portions are sewn together at the seam.

5. The wound dressing garment of claim 3, wherein said first and second panels of said structure layer are fused together at the seam.

6. The wound dressing garment of claim 2, wherein said first and second edge portions have complementary shapes corresponding to a contour of the portion of the body.

7. The wound dressing garment of claim 2, further comprising a fastener in communication with the third and fourth edge portions of said structure layer, said fastener being adapted to detachably secure the third and fourth edge portions to each other.

8. The wound dressing garment of claim 1, wherein said gel layer comprises at least one sheet of a gel material.

9. The wound dressing garment of claim 1, wherein said gel layer comprises a silicone gel that leaves no perceptible residue on the skin surface when removed.

10. The wound dressing garment of claim 1, wherein said gel layer comprises one of a hydrogel gel and a polyurethane gel.

11. The wound dressing garment of claim 1, wherein said gel layer is in direct contact with said structure layer.

12. The wound dressing garment of claim 1, wherein said gel layer is bonded to said structure layer by at least one of: heat, pressure, an adhesive, and a self-adhesiveness of the gel layer.

13. The wound dressing garment of claim 1, further comprising an intervening layer dispose between said structure layer and said gel layer.

14. The wound dressing garment of claim 13, wherein said intervening layer comprises an elastomeric material.

15. The wound dressing garment of claim 13, wherein said intervening layer is bonded to said structure layer by at least one of: heat, pressure, and an adhesive.

16. The wound dressing garment of claim 13, wherein said intervening layer is detachable from said structure layer over substantially all of said garment.

17. The wound dressing garment of claim 1, wherein the garment is suitable for enveloping at least a portion of at least one of: a finger, a hand, a wrist, an elbow, a shoulder, an arm, the head, the scalp, the face, the neck, the torso, the waist, the groin, a hip, a leg, a knee, an ankle, a foot, and a toe.

18. The wound dressing garment of claim 1, further comprising a peelable protective layer formed on the interior surface of the garment.

19. A method of forming a wound dressing garment that adheres to the skin of the wearer and directly contacts a skin wound to promote healing of the skin wound, the method comprising the steps of:

(a) forming a structure layer of a pliable material to envelope a body portion including an external skin wound to dress that wound and promote healing, the structure layer including an inner surface that faces generally toward the skin of the wearer when the garment is worn on the body and first, second, third and fourth edge portions, wherein at least the first and second edge portions are securable to each other to provide a partial enclosure suitable for enveloping said body portion; and (b) coupling to the structure layer a self-adhesive gel layer suitable for directly contacting said external skin wound to promote said healing, wherein said gel layer serves as said inner surface and forms an interior surface of the garment and said gel layer is separable from said structure layer along at least one of the third and fourth edge portions of said structure layer, such that edge portions of said gel layer and the third and fourth edge portions of said structure layer are independently overlappable, and, when the edge portions of said gel layer are overlapped and the third and fourth edge portions of said structure layer are secured to each other in an overlapped fashion, both the third and fourth edge portions of said structure layer overlay the edge portions of said gel layer.

20. The method of claim 19, wherein step (a) includes permanently securing together the first and second edge portions along a seam in a substantially non-overlapping manner.

21. The method of claim 20, wherein step (a) further includes forming the structure layer from at least a first panel having the first edge portion and a second panel having the second edge portion.

22. The method of claim 20, wherein step (a) further includes forming the structure layer from a fabric material, and the first and second edge portions being sewn together at the seam.

23. The method of claim 21, wherein step (a) further includes fusing together the first and second panels of the structure layer at the seam.

24. The method of claim 20, wherein step (a) further includes shaping the first and second edge portions to have complementary shapes corresponding to a contour of the portion of the body.

25. The method of claim 20, wherein the method further comprises the step of:

(c) providing a fastener in communication with the third and fourth edge portions of the structure layer, the fastener being adapted to detachably secure the third and fourth edge portions to each other.

26. The method of claim 19, wherein step (b) includes forming the gel layer from at least one sheet of a gel material.

27. The method of claim 19, wherein step (b) includes forming the gel layer from a silicone gel that leaves no perceptible residue on the skin surface when removed.

28. The method of claim 19, wherein step (b) includes forming the gel layer from one of a hydrogel gel and a polyurethane gel.

29. The method of claim 19, wherein step (b) includes forming the gel layer to be in direct contact with the structure layer.

30. The method of claim 19, wherein step (b) includes bonding the gel layer to the structure layer by at least one of: heat, pressure, an adhesive, and the self-adhesiveness of the gel layer.

31. The method of claim 19, further comprising the step of:
 (c) providing an intervening layer between the structure layer and the gel layer.

32. The method of claim 31, wherein step (c) includes forming the intervening layer from an elastomeric material.

33. The method of claim 31, wherein step (c) includes bonding the intervening layer to the structure layer by at least one of: heat, pressure, and an adhesive.

34. The method of claim 31, wherein step (c) includes forming the intervening layer to be separable from the structure layer over substantially all of the garment.

35. The method of claim 19, wherein the garment is formed to envelop at least a portion of at least one of: a finger, a hand, a wrist, and elbow, a shoulder, an arm, the head, the scalp, the face, the neck, the torso, the waist, the groin, a hip, a leg, a knee, an ankle, a foot and a toe.

36. The method of claim 19, further comprising the step of:
 (c) providing a peelable protective layer on the interior surface of the garment.

37. A method of treating a wound on the skin of a body by applying to the wound a wound dressing garment comprising: a pliable structure layer including at least first and second edge portions securable to each other to provide a partial enclosure; and a self-adhesive gel layer coupled to the structure layer to serve as an inner structure layer surface and form an interior surface of the garment, the gel layer being separable from the structure layer along at least one of the first and second edge portions such that edge portions of said gel layer and the first and second edge portions of said structure layer are independently overlappable, the method comprising the steps of:
 (a) dressing the wound by enveloping with the wound dressing garment a portion of the body on which an external skin wound is present;
 (b) bringing the gel layer into direct contact with the external skin wound and skin surrounding the wound, the gel layer adhering to the skin surrounding the wound, thereby securing the wound dressing garment to the portion of the body and promoting healing of the wound; and
 (c) overlapping edge portions of the gel layer and securing the first and second edge portions of the structure layer to each other in an overlapped fashion such that the first and second edge portions of the structure layer overlay edge portions of the gel layer.

38. The method of claim 37, further comprising the step of:
 (d) detachably securing the first and second edge portions of the structure layer to each other using fasteners.

39. The method of claim 38, wherein step (d) includes detachably securing the first and second edge portions in an overlapped manner.

40. The method of claim 37, wherein step (a) includes enveloping at least a portion of at least one of: a finger, a hand, a wrist, an elbow, a shoulder, an arm, the head, the scalp, the face, the neck, the torso, the waist, the groin, a hip, a leg, a knee, an ankle, a foot and a toe.

41. The method of claim 37, further comprising the step of:
 (d) customizing the wound dressing garment to a particular wound by trimming off a portion of the gel layer unnecessary for treating the wound.

42. The method of claim 37, wherein step (b) includes bringing into contact with the wound a silicone gel that leaves no perceptible residue on the skin surface when removed.

43. A wound dressing garment for promoting the healing of skin wounds, comprising:
 a structure layer formed of a pliable material to envelope a body portion including an external skin wound to dress that wound and promote healing, said structure layer including an inner surface that faces generally toward the skin of the wearer when the garment is worn on the body and at least first and second edge portions that are securable to each other to provide a partial enclosure suitable for enveloping said body portion; and
 a self-adhesive gel layer suitable for directly contacting said external skin wound to promote said healing, said gel layer being coupled to said structure layer and serving as said inner surface to form an interior surface of the garment;
 wherein said gel layer is separable from said structure layer along at least one of the first and second edge portions of said structure layer, such that edge portions of said gel layer and the first and second edge portions of said structure layer are independently overlappable and, when the edge portions of said gel layer are overlapped and the first and second edge portions of said structure layer are secured to each other in an overlapped fashion, both the first and second edge portions of said structure layer overlay the edge portions of said gel layer.

44. The wound dressing garment of claim 43, wherein said wound dressing garment further comprises:
 a fastener in communication with the first and second edge portions of said structure layer, said fastener being adapted to detachably secure the first and second edge portions to each other.

45. The wound dressing garment of claim 43, wherein said structure layer comprises at least a first panel including the first edge portion and a second panel including the second edge portion.

46. The wound dressing garment of claim 43, wherein said structure layer comprises a fabric material.

47. The wound dressing garment of claim 46, wherein said structure layer comprises a mesh material.

48. The wound dressing garment of claim 43, wherein said structure layer comprises an elastomeric material.

49. A method of forming a wound dressing garment that adheres to the skin of the wearer and directly contacts a skin wound to promote healing of the skin wound, the method comprising the steps of:
 (a) forming a structure layer of a pliable material to envelope a body portion including an external skin wound to dress that wound and promote healing, the structure layer including an inner surface that faces generally toward the skin of the wearer when the garment is worn on the body and first and second edge portions that are securable to each other to provide a partial enclosure suitable for enveloping said body portion; and (b) coupling to the structure layer a self-adhesive gel layer suitable for directly contacting said external skin wound to promote said healing, wherein said gel layer serves as said inner surface and forms an interior surface of the garment and said gel layer is separable from said structure layer along at least one of the first and second edge portions of said structure layer, such that edge portions of said gel layer and the first and second edge portions of said structure layer are independently overlappable and, when the edge portions of said gel layer are overlapped and the first and second edge portions of said structure layer are secured to each other in an overlapped fashion, both the first and second edge portions of said structure layer overlay the edge portions of said gel layer.

50. The method of claim 49, further comprising:

(c) providing a fastener in communication with the first and second edge portions of said structure layer, said fastener being adapted to detachably secure the first and second edge portions to each other.

51. The method of claim 50, wherein step (a) includes forming the structure layer from at least a first panel having the first edge portion and a second panel having the second edge portion.

52. The method of claim 50, wherein step (a) includes forming the structure layer from a fabric material.

53. The method of claim 52, wherein step (a) includes forming the structure layer from a mesh material.

54. The method of claim 50, wherein step (a) includes forming the structure layer from an elastomeric material.

* * * * *